US005145785A

United States Patent [19]
Maggard et al.

[11] Patent Number: 5,145,785
[45] Date of Patent: Sep. 8, 1992

[54] DETERMINATION OF AROMATICS IN HYDROCARBONS BY NEAR INFRARED SPECTROSCOPY AND CALIBRATION THEREFOR

[75] Inventors: Steven M. Maggard, Huntington, W. Va.; William T. Welch, Ashland, Ky.

[73] Assignee: Ashland Oil, Inc., Ashland, Ky.

[21] Appl. No.: 626,132

[22] Filed: Dec. 11, 1990

[51] Int. Cl.[5] .................. G01N 21/00; G01N 33/26
[52] U.S. Cl. ............................. 436/8; 250/252.1; 250/301; 250/304; 250/339; 436/52; 436/55; 436/60; 436/140; 436/164; 436/171
[58] Field of Search ............... 436/8, 52, 60, 140, 436/161, 164, 171, 174, 177, 178, 55; 250/252.1, 301, 304, 339, 341, 343

[56] References Cited

U.S. PATENT DOCUMENTS

| | | | |
|---|---|---|---|
| 4,277,326 | 7/1981 | Schlosberg et al. | 208/263 |
| 4,323,777 | 4/1982 | Baskins | 250/339 |
| 4,433,239 | 2/1984 | Thompson | 250/255 |
| 4,591,718 | 3/1986 | Amer | 250/339 |
| 4,800,279 | 1/1989 | Hieftje et al. | 250/339 |
| 4,866,983 | 9/1989 | Vinegar et al. | 436/31 X |
| 4,920,792 | 5/1990 | DiFoggio | 436/31 X |
| 4,963,743 | 10/1990 | Satake et al. | 250/339 |

FOREIGN PATENT DOCUMENTS

| | | |
|---|---|---|
| 0285251 | 5/1988 | European Pat. Off. . |
| 0304232 | 2/1989 | European Pat. Off. . |
| 0305090 | 3/1989 | European Pat. Off. . |
| 2217838 | 11/1989 | United Kingdom . |

OTHER PUBLICATIONS

"Advances in Near Infrared Analyzer Technology", Dr. H. Mark & Dr. G. Kemeny, Feb. 1991, Chemical Processing, pp. 54–58.

LT Appl. Nste. Industry: Petroleum, "Determination of Octane Number by NIR", LT Industries, Rockville, Md.

"Nondestructive Analytical Proc. for Simultaneous Estimation of the Major Classes of Hydrocarbon Constituents of Finished Gasolines," Kelly et al., Anal. Chem. 1990, 62, pp. 1444–1451.

*Primary Examiner*—Robert J. Hill, Jr.
*Attorney, Agent, or Firm*—Richard C. Willson, Jr.; Stanley M. Welsh

[57] ABSTRACT

Mid-distillate hydrocarbon fuels, preferably having initial boiling points above 350° F., are separated e.g. by prep-HPLC into non-aromatic and aromatic fractions which are used to set 0% aromatics (the non-aromatics) and 100% aromatics (the aromatics) on an NIR spectrophotometer. From NIR aromatic band absorbances of unknown samples, their percent aromatics is determined using this two-point calibration and the Beer-Lambert equation. Preferred NIR bands of 1650–1700 and 2120–2256 exhibit excellent correlation with aromatics content.

17 Claims, 8 Drawing Sheets

DETERMINATION OF AROMATICS IN HYDROCARBONS BY NEAR INFRARED SPECTROSCOPY AND CALIBRATION THEREFOR

CROSS REFERENCES TO RELATED APPLICATION

U.S. patent application Ser. No. 506,391, filed Apr. 9, 1990 by S. M. Maggard (docket number 6362AUS) relates to the determination of PIANO components in hydrocarbons by near infrared spectroscopy and is therefore related to the field of the present invention.

BACKGROUND OF THE INVENTION

I. Field of the Invention

The present invention relates to the determination of aromatic constituents in hydrocarbons by near infrared spectroscopy and is generally classified in U.S. Patent Office Class 250, subclass 343, 341, and 339.

II. Description of the Prior Art

U.S. Pat. No. 4,963,745 granted Oct. 16, 1990 for octane measuring process and device to S. M. Maggard teaches the use of near infrared absorbance of the methyne band to measure octane, etc. of a fuel by near infrared spectroscopy.

The aforementioned Ser. No. 506,391 teaches the determination of the constituents of PIANO aromatics (paraffins, aromatics, isoparaffins, naphthenes, and olefins) by near infrared techniques.

U.S. Pat. No. 4,800,279, and the references cited thereon, to Hieftje et al. relates to the determination of properties of hydrocarbons by near infrared absorbance.

European Patent Office 0285 251 published October, 1988 relates to the general field of analysis by near infrared spectroscopy.

"Near-Infrared Reflectance Analysis by Gauss-Jordan Linear Algebra", D. E. Honigs, J. M. Freelin, G. M. Hieftje, T. B. Hirschfeld, Applied Spectroscopy, vol. 37, no. 6, 1983, pp 491–497, teaches statistical manipulation of NIR spectral data.

"Prediction of Gasoline Octane Numbers from Near Infrared Spectral Features in the Range 660–1215 nm" by J. J. Kelly et al., Analytical Chemistry, vol. 61, no. 4, Feb. 15, 1989, pp 313–320, relates to the prediction of octane. Also by Kelly et al., "Nondestructive Analytical Procedure for Simultaneous Estimation of the Major Classes of Hydrocarbon Constituents of Finished Gasolines", Analytical Chemistry, vol. 62, no. 14, Jul. 15, 1990, pp 1444–1451.

Percents of each of the individual compounds detected by gas chromatography are grouped under their respective generic classifications in the PIANO classification system, and the relative percentage of each of the components paraffins through olefins is determined in weight percent, volume percent, or mole percent as required. An example of this procedure is that taught by Analytical Automation Specialists, Inc., "The Detailed Analysis of Petroleum Naphthas, Reformates, Gasoline and Condensates by High-Resolution Gas Chromatography", Operators Manual, P.O. Box 80653, Baton Rouge, La. 70898. Also available is AAS (Analytical Automated Systems) PIANO Software Package, Sievers Research PIANO Software Package.

Other NIR analysis techniques are taught in J. Prakt. Chem., 317(1), 1–16 by Bernhard and Berthold, who perform structural group analysis of mixtures of saturated and aromatic hydrocarbons, and in the quantitative analysis of benzene-toluene-paraffin mixtures in the near-infrared by Leimer and Schmidt in Chem. Tech. (Leipzig), 25(2), 99–100.

"Near-infrared spectroscopy of hydrocarbon functional groups was performed by Tosi and Pinto, Spectrochim ACTA, Part A, 28(3), 585–97, who examined 50 linear and branched paraffins and related the absorbtivities to the concentration of the groups such as $CH_3$ and $CH_2$.

Ultraviolet and near-infrared analysis of mixtures of aromatics is taught by Schmidt in Erdoelkohle, Erdgas, Petrochem., 21 (6), 334–40, who sought to determine concentrations of specific compounds.

Hydrotreating is taught by many chemical engineering texts. "Reduction of Aromatics in Diesel Fuel" by A. J. Suchanek, National Petroleum Refiners Association, AM-90-21, 1990, provides a brief review.

Other patents which relate to the general field of the invention are U.S. Pat. Nos. 4,277,326; 4,264,336; 3,496,053; 903,020; 4,323,777; 4,433,239; and 4,591,718.

Each of the above references is understood to teach a correlation between the absorbance in the near infrared and some physical or chemical property. None of them teach an absolute determination for a very complex mixture such as diesel fuel, as is involved in the percent aromatics determined by the present invention.

Also none of the references teach the determination of aromatics where GC separations are not possible due to co-elution.

SUMMARY OF THE INVENTION

I. General Statement of the Invention

Figure 1:
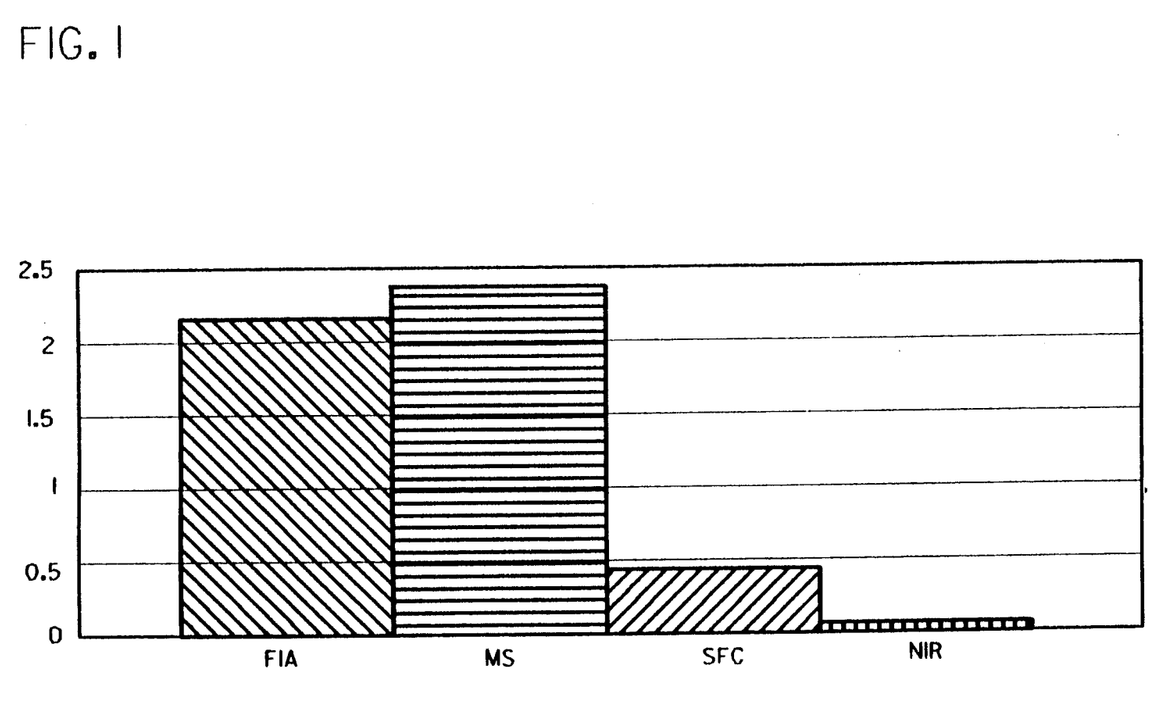
FIG. 1 is a comparison of the repeatability error (% by absolute error) of four analytical methods for determining aromatics in diesel fuels (no. 2 fuel oil). The methods compared are fluorescent indicator absorption (FIA) by ASTM D-1319; mass spectroscopy (MS); super fluid chromatography (SFC) in which CO2 above its critical pressure and temperature is used as the eluent; and near infrared according to the techniques of the present invention (NIR) for sets of 6 identical samples. This figure shows the excellent repeatability of the techniques of the present invention. (All determinations are in wt. % except FIA is in vol. %.)
Figure 2:
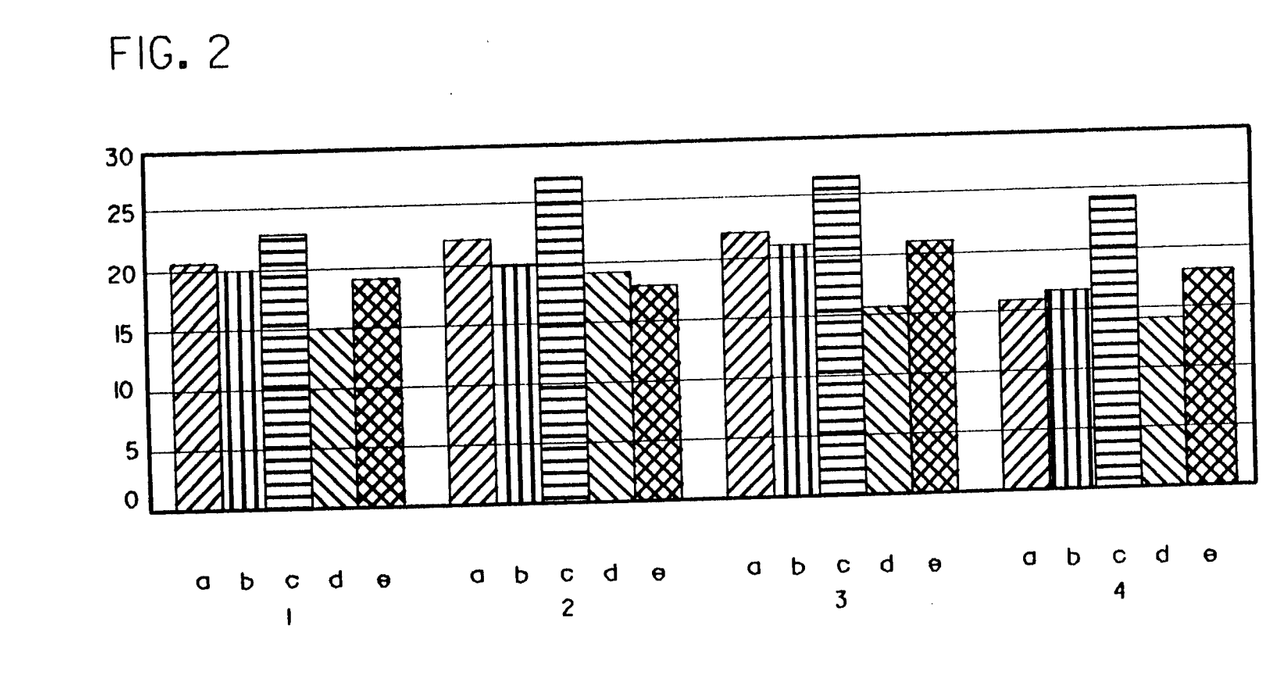
FIG. 2 is a comparison of the percent aromatics determined in identical sets of 4 samples by heated FIA (a), heated FIA plus water deactivation of the chromatographic column (b), SFC (c); HPLC/DCD (high performance liquid chromatography using a dielectric constant-measuring detector) (d); and the NIR of the present invention (e). Note that results are expressed in volume percent for the two FIA methods and the HPLC/DCD method, whereas SFC and NIR results are expressed in weight percent. Note that NIR (except in sample no. 2) is closest to the average of all methods combined.
Figure 3:
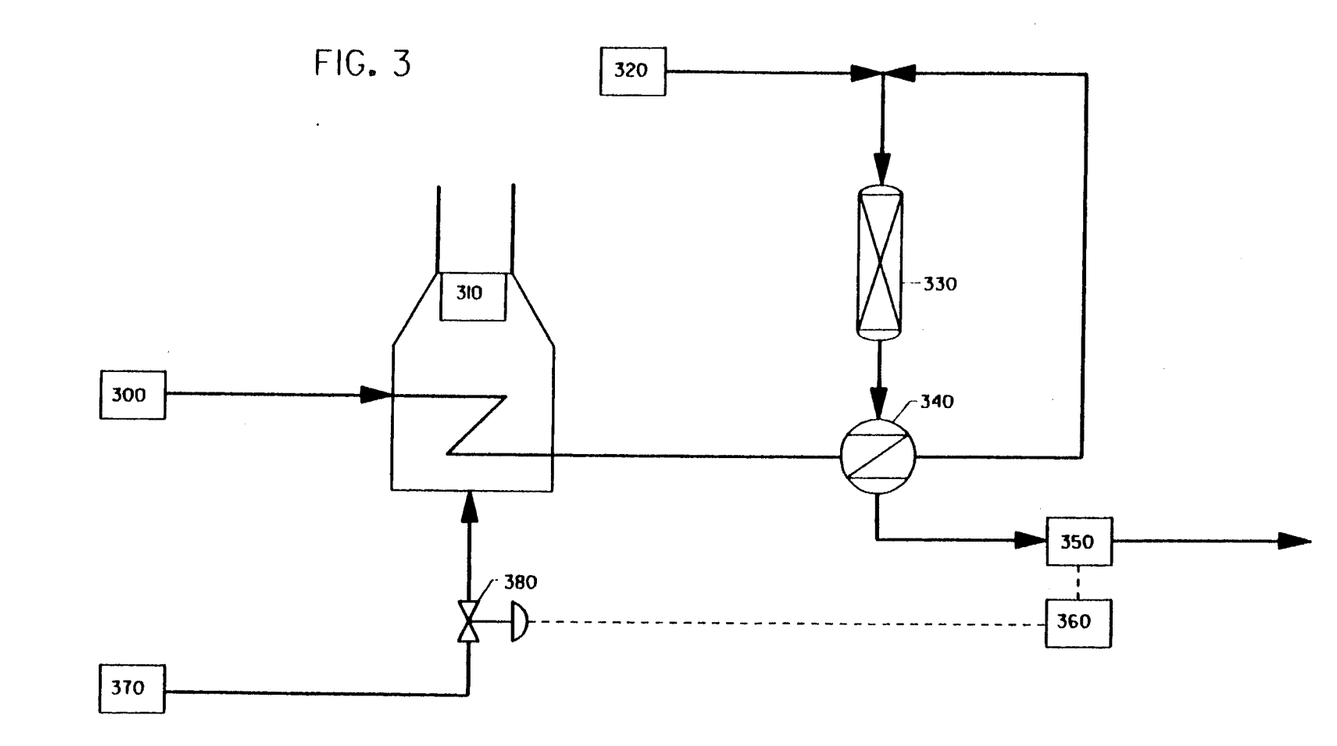
FIG. 3 is a schematic diagram of a control system utilizing the NIR techniques of the present invention to control a refinery hydrogenation unit in which sufficient hydrogen is added not only to combine with the sulfur, but also sufficient to cause scisson and destruction of aromatics in diesel fuel.

According to the present invention, the absolute concentration of aromatics is determined for mixtures with other hydrocarbons, preferably fuels, and most preferably diesel fuels, all grades, kerosene, fuel oils, all grades, light cycle oil, light vacuum oil, heating oils and vacuum oils as known in the petroleum industry. By measuring the absorption at a frequency in the range of 800–2500 nm (nanometers), most preferably from 1650–1700 or 2120–2256 nm, then correcting for the absorption due to non-aromatics in the sample at that frequency and, by data resolution, determining the absolute value of (or percent) aromatics in the sample. The invention can be practiced on a batch basis as in laboratory cells, or by a flow basis, e.g. by using fiber optic or other probes, and can be used for direct or indirect control of process variables such as hydrogen uptake, as illustrated in FIG. 3.

Standardization is an important feature of the present invention and is accomplished by separating the aromatics from the non-aromatics in the sample by use of well-known preparative high performance liquid chromatography, e.g. as described in Petroleum Derived Hydrocarbons, John D. Bacha, John W. Newman, and J. L. White, ACS Symposium series 303, Chapter 6.

The concentration of the aromatics in the sample is then determined by measuring the absorbance of each of the two portions at the frequency being used (e.g. 1672 nm) and the absorbance of the aromatic fraction can be (but does not have to be) corrected by subtracting the absorbance of the non-aromatic fraction. The resulting solution of the equation:

$$Y = mX + b + e$$

can be used to determine the percent aromatics of many successive samples so long as the molecular constituents remain approximately the same, thus, for diesel fuel the preferred hydrocarbon mixture to be measured, only one standardization is needed for a long period and many analyses.

In the above equation:
m = the slope of the line (by the standard)
X = the absorbance of the aromatics
b = a constant which is determined by the fitting of the absorbance against the absolute weight values obtained above.
Y = percent aromatics
e = any error in the determination The elements of the invention are therefore preferably the determination of aromatics content in hydrocarbons, preferably in the diesel no. 2 fuel oil boiling range by:

(a) separating the aromatics from the non-aromatics (saturates and olefins) in a representative sample, to be used as a calibrating standard, preferably by preparatory high performance liquid chromatograph ("prep.HPLC");

(b) measuring NIR absorbance of the resulting non-aromatics and aromatic portions (or of prepared known homogenous mixtures) derived from the above sample;

(c) deriving the calibration equation and its constants by Beer-Lambert's Law or other well-known spectral data resolution techniques;

(d) measuring the NIR absorbance of a representative sample using the above calibration equation, determine the aromatic and/or the non-aromatic content.

II. Utility of the Invention

The present invention, as described above, can be utilized for most fuels, preferably for diesel fuel, and preferably by measuring absorbance at a frequency in the range of 800–2500 nm, most preferably 1650–1700 nm or 2120–2256 nm. The invention can be utilized as a batch process, in a flow-through cell, by the use of fiberoptic probes either bundled or single fiber, and the process control can be either feed-back or feed-forward based on the samples absorbance in the near-infrared, or optionally the first derivative of the samples absorbance or some other mathematical function of absorbance, being employed e.g. to operate a control valve.

Increasing governmental regulation and environmental laws are impacting the permissible percentage of aromatics tolerated in diesel fuels, turbine fuels, kerosene, heating oils, and other oils.

Therefore, the need for accurate, absolute determinations of the present invention, particularly for on-line control of aromatics in fuels is increasing rapidly.

DESCRIPTION OF THE PREFERRED EMBODIMENTS

EXAMPLE 1

The Invention Using Batch-Type NIR Cells

A diesel fuel sample (6 grams) is separated into its aromatic and non-aromatic fractions by passing (500 ml./minute) the fuel down a silica diamine column connected in series to a silica gel column using hexane as the solvent on a Waters Div. Millipore, Milford, Mass., Model 500A high performance liquid chromatograph. The saturate fraction is collected off the end of the column and the hexane mobile phase is removed by rotary evaporation. The aromatics are then back flushed from the column by reversing the flow and substituting methylene chloride as the solvent. The solvent is again removed by rotary evaporation.

The near infrared absorbance spectra of the non-aromatic and aromatic fractions (or known proportions thereof) are measured on an NIR Systems, Inc., Model 6500 spectrophotometer at 1672 nm and assigned concentrations of 0% and 100% aromatics by weight, respectively.

An equation of the form
Y=mX+b is calculated from Beer-Lambert Law,
where Y is the aromatic concentration, X is the
absorbance, m is the slope of the regression line,
and b is its Y-intercept.

Figure 7:
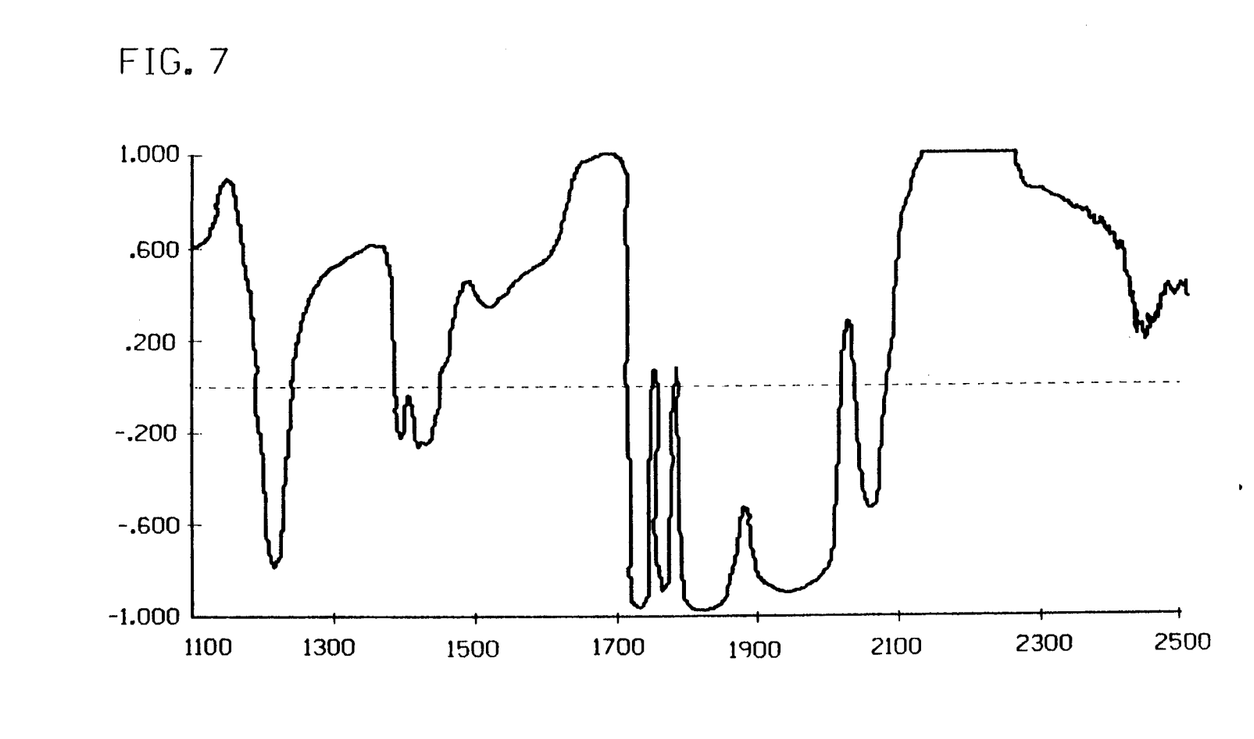
FIG. 7 is a plot showing the correlation observed at each wavelength from 1100–2500 nm for the aromatic content of diesel fuels using the techniques of the current invention. Note the superior correlation discovered at 1650 to 1700 nm and at 2120 to 2256 nm, most preferably 1654 to 1696 nm, or 2124 to 2252 nm, or both.
Figure 8:
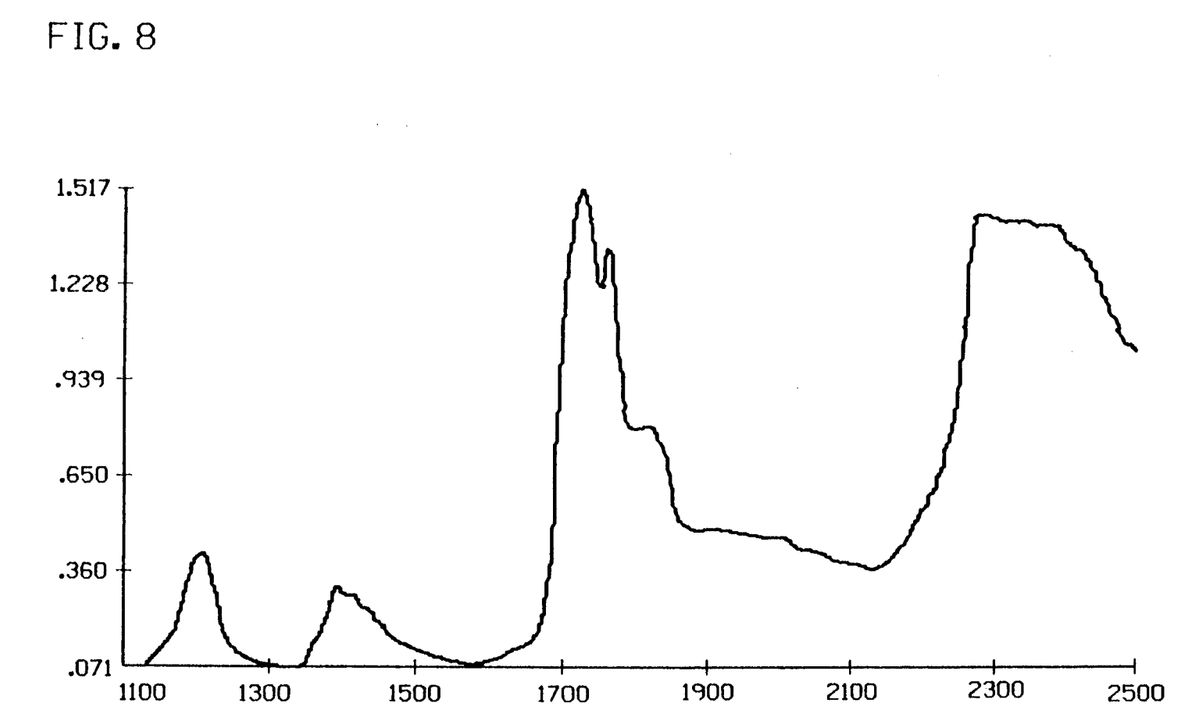
FIG. 8 is a near infrared absorbance spectrum of the non-aromatic fraction of diesel fuel which was obtained by HPLC.

The absorbances of a series of five unknown diesel fuel samples are measured and, using the above equation and the sample's absorbance at 1672 nm, aromatic concentration of each sample is calculated and the correlations are plotted together as FIG. 7. Note the near perfect correlation in the preferred bands of the invention.

EXAMPLE 2

Flow-Through Mode

When the techniques of Example 1 are employed using fiberoptic probes to measure flowing streams and side streams in a refinery diesel fuel stream, accuracy approximately as good as obtained in the batch-process of Example 1 is achieved. Fiber optical probes preferably use the NIR range of 1650 to 1700 nm because of the cost and difficulty in obtaining non-absorbing fiber probes which transmit in the range of 2124 to 2252 nm.

EXAMPLE 3

The Invention Controlling a Process

Figure 4:
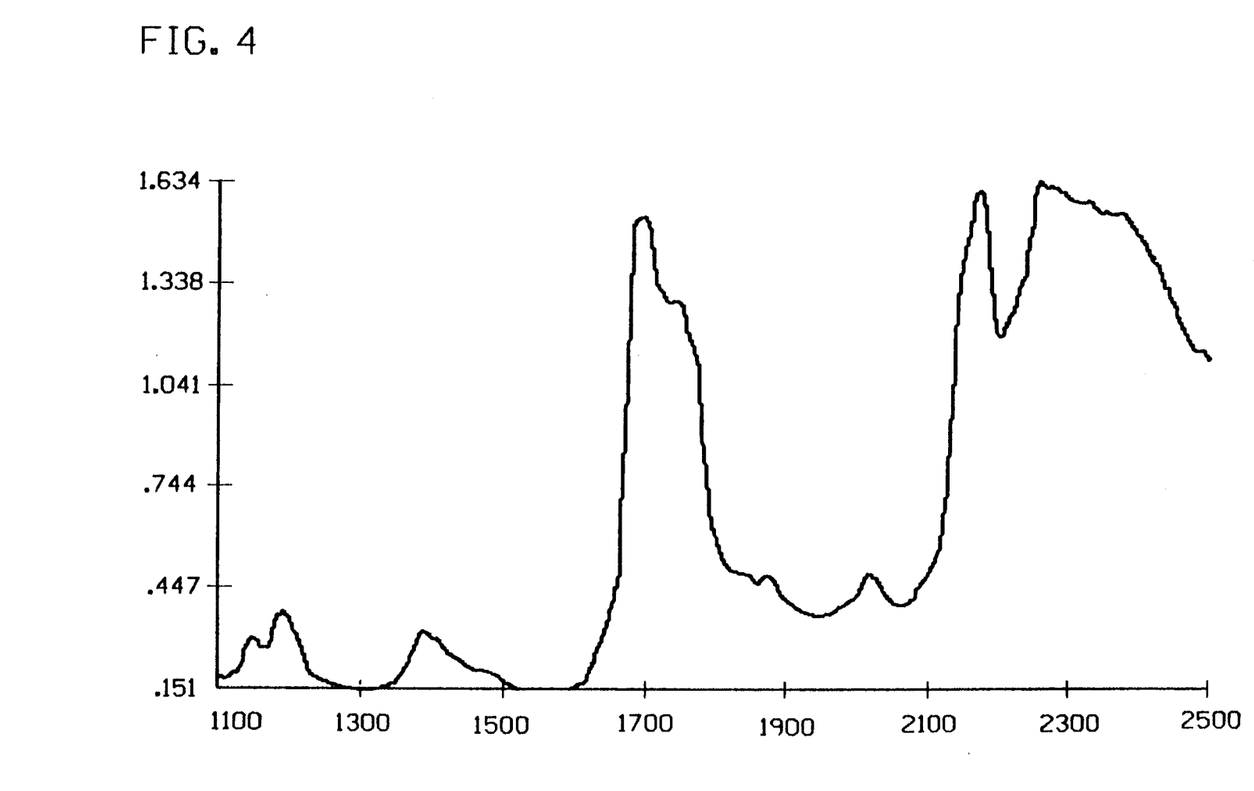
FIG. 4 is a near infrared absorbance spectrum of the aromatic fraction of a diesel fuel which was obtained by HPLC.

FIG. 3 schematically shows an important process control application of this invention. New diesel fuel regulations require that highway fuel produced after October, 1993, meet a minimum cetane number specification. Cetane number and aromatics are closely related, as shown for example in FIG. 4. "Reduction of Aromatics in Diesel Fuel", A. J. Suchanek, in National Petroleum Refiners Association, AM-90-21, 1990. By use of this or similar relations, and an NIR instrument calibrated as according to this invention, very close control of hydrotreater operation can be attained at minimum severity and hydrogen consumption. Raw feed, stream 300, flows through fired heater 310, feed/effluent exchanger 340, is admixed with hydrogen stream 320, through an adiabatic hydrotreating reactor 330, to tankage. Aromatic content of the stream is measured by NIR probe 350, and this information provided to the process control computer 360. Conversion of aromatics content to estimated cetane number is made by the computer, and the flow of fuel stream 370 to the fired heater is adjusted as necessary by control valve 380. For instance, aromatics levels are higher and cetane number is lower in the fired heater and at a lower reactor temperature. This lower temperature reduces the aromatics saturation reaction rate, increasing the aromatic content (decreasing the cetane number) of the diesel product. This results in a savings in hydrogen consumption, fuel, and other utilities. In the case of measured cetane number less than 40, a similar chain of events results in higher hydrotreating severity and reduced in the effluent product aromatics. This on-line control allows rapid, very close control of product quality and eliminates present problems with production of off-spec finished products in quantities because corrections are implemented much sooner. This also results in a close-specification diesel fuel which is in much demand in today's marketplace.

EXAMPLE 4

Controlling Hydrotreater Severity

Figure 5:
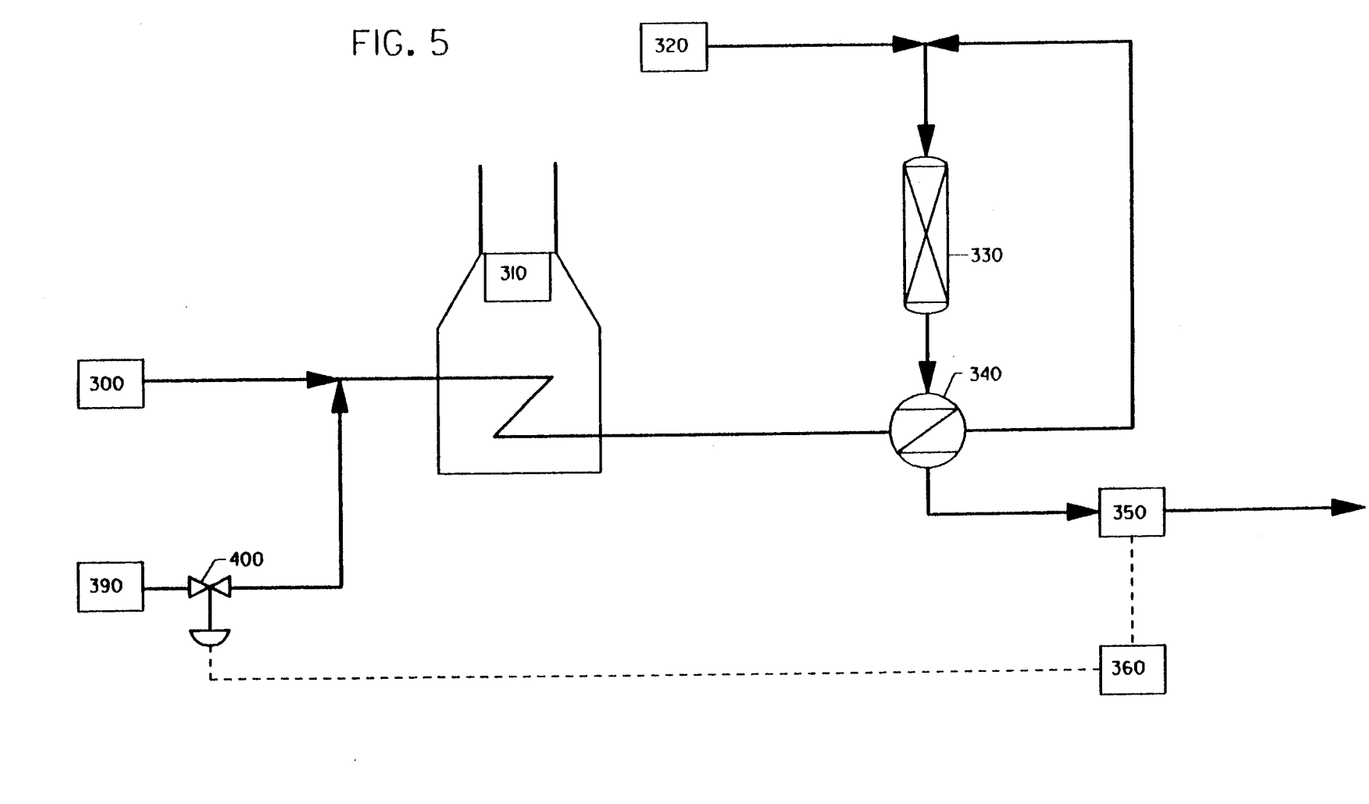
FIG. 5 shows a schematic control system as detailed in Example 4.
Figure 6:
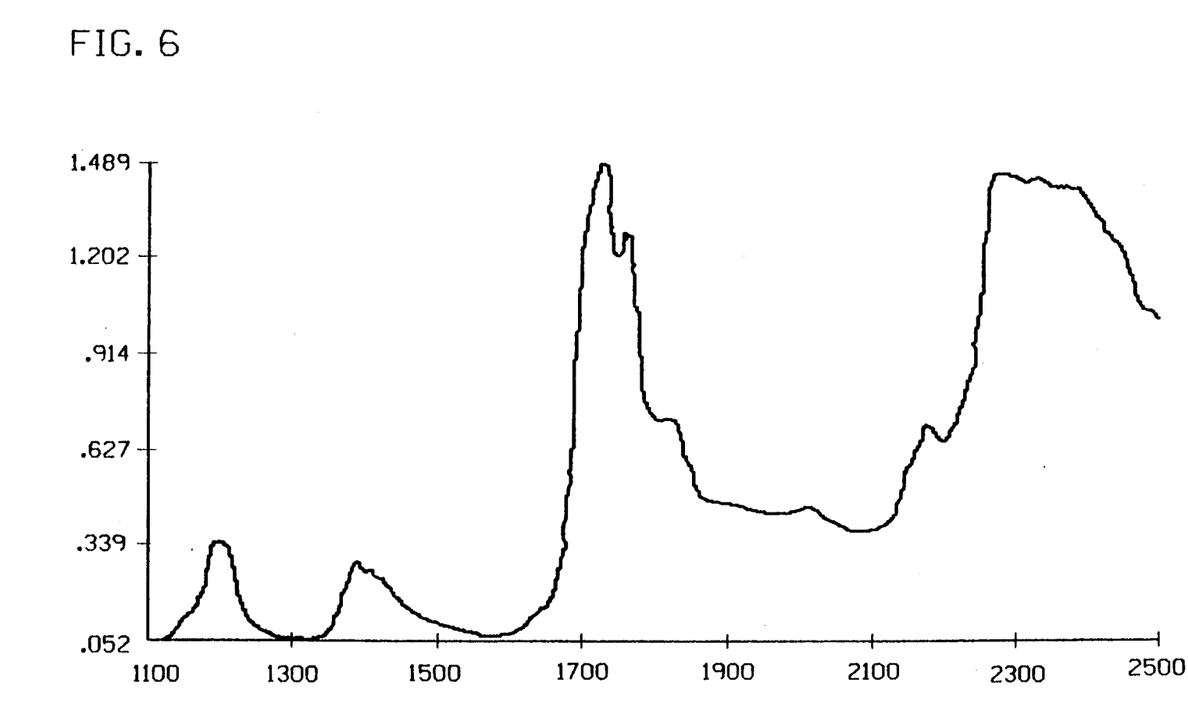
FIG. 6 is a near infrared absorbance spectrum of a typical diesel fuel.

Additional process control advantages of the invention are exemplified in FIG. 5. For the same hydrotreating scheme shown in FIG. 3 (Example 3), this invention can allow maximum use of aromatic components in diesel fuel such as FCC LCO while operating the hydrotreater at maximum severity when aromatic/cetane limits are reached. Maximum use of FCC LCO (light cycle oil, high in aromatics) in diesel is advantageous to the refiner due to its relatively low alternate value, but it is a major contributor to the aromatics content of the diesel pool. In FIG. 5, on-line NIR analysis allows maximum FCC LCO flow by maintaining constant analysis of the product diesel stream, providing information to the aforementioned process control computer 360 which adjusts FCC LCO flow 390 through flow control valve 400 such that the product stream just meets the required aromatics/cetane specification. This application is particularly attractive in that hydrotreating catalyst deactivation will be automatically compensated by the control loop by reducing the quantity of FCC LCO blended as the catalyst activity declines over the normal aging cycle.

EXAMPLE 5

Control of Aromatics in Solvents

Manufacture of Low Odor Base Solvent (LOBS) is accomplished by the control schematic of FIG. 3. An NIR probe, properly calibrated for 0–5% aromatics, is used to directly control product quality (low aromatic content) to meet the specification level, by hydrotreatment. Blending also can be controlled by NIR, preferably using feed-forward of the aromatics content of the feed as measured by NIR.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

Reference to documents made in the specification is intended to result in such patents or literature being expressly incorporated herein by reference including any patents or other literature references cited within such documents.

What is claimed is:

1. A process for measuring the aromatics content of hydrocarbons using a near infrared spectrophotometer comprising in combination the steps of:
    a. selecting a sample generally representative of said hydrocarbons;
    b. separating out a non-aromatic hydrocarbon portion from an aromatics portion of said sample;
    c. measuring the absorbance of said aromatics portion and said non-aromatics portion or a portion containing known mixed proportions of aromatics, and/or saturates, and/or olefins, in the range of 1650–1700 or 2120–2256 nm;
    d. by Beer-Lambert's Law or other methods of data resolution, calibrating said near infrared spectrophotometer or a related computer receiving a signal from the spectrophotometer to provide a signal indicative of the concentration of aromatics, or non-aromatics, in at least one additional hydrocarbon sample;
    e. thereafter measuring the absorbance of the same or a different hydrocarbon sample with said calibrated spectrophotometer in at least one of said ranges; and
    f. determining the aromatics content of said same or different sample from its absorbance.

2. A process according to claim 1 wherein the separation of the aromatics portion from the non-aromatics portion is accomplished by chromatography.

3. A process according to claim 1 wherein the separation of the aromatics portion from the non-aromatics portion is accomplished by preparatory high performance liquid chromatography.

4. A process according to claim 1 wherein the data resolution step involves solving the equation:

$$Y = mX + b + e$$

For a constant pathlength where:
Y = concentration of aromatics (or saturates)
m = the slope of the line (by the portions)
X = the absorbance of aromatics
b = the Y-intercept
e = any error in the measurements.

5. A process according to claim 1 wherein the hydrocarbons are analyzed by the near infrared spectrophotometer using batch cells.

6. A process according to claim 1 wherein the hydrocarbons are analyzed by the near infrared spectrophotometer using flow-through means.

7. A process according to claim 1 wherein the hydrocarbons are analyzed by the near infrared spectrophotometer using probes.

8. A process according to claim 1 wherein the hydrocarbons are analyzed by the near infrared spectrophotometer using fiber optic probes.

9. A process according to claim 1 wherein the hydrocarbons are analyzed by the near infrared spectrophotometer using a fiber optic probe.

10. A process according to claim 1 in which the aromatics content is measured for a diesel fuel or kerosene.

11. A process according to claim 1 wherein the wavelength measured is in the range of 1650-1700 nanometers.

12. A process according to claim 1 whereby another wavelength or wavelengths are used in combination.

13. A process according to claim 1 whereby the near infrared signal being processed is a mathematical function or a combination of mathematical functions of the absorbance spectrum of the aromatics or non-aromatic portion.

14. A process according to claim 1 wherein said samples is produced by combining different diesel fuels prior to the separation into aromatic and non-aromatic fractions or where the aromatic and non-aromatic fractions obtained from different diesel fuels are combined and used as the aromatic and non-aromatic fractions.

15. A process according to claim 1 wherein said samples is obtained from the same or a different diesel fuel.

16. A process according to claim 1 in which a fuel is blended to a desired aromatic content based on NIR measurements.

17. A process of calibrating or recalibrating a near infrared spectrophotometer for measurement of aromatics content of hydrocarbons comprising in combination the steps of:
 a. selecting a first sample generally representative of said hydrocarbons;
 b. separating out the non-aromatic hydrocarbon portion from the aromatic portion of said first sample;
 c. measuring in a first spectrophotometer the absorbance of said aromatics portion and said non-aromatics portion or a portion containing known mixed proportions of aromatics, and/or saturates, and/or olefins, in the range of 1650-1700 or 2120-2256 nm;
 d. by Beer-Lambert's Law or other methods of data resolution, calibrating said first near infrared spectrophotometer or related computer receiving a signal from the spectrophotometer;
 e. calibrating a second spectrophotometer or related computer or re-calibrating said first spectrophotometer or related computer, referencing such instrument to a sample measured in steps c. and d., and adjusting said instrument to provide a value equal to the value obtained in steps c. and d.

* * * * *